United States Patent
Van Rheenen

[11] 3,965,118
[45] June 22, 1976

[54] LACTONE INTERMEDIATES

[75] Inventor: Verlan H. Van Rheenen, Kalamazoo, Mich.

[73] Assignee: The Upjohn Company, Kalamazoo, Mich.

[22] Filed: Apr. 19, 1974

[21] Appl. No.: 462,234

Related U.S. Application Data

[62] Division of Ser. No. 273,785, July 21, 1972, Pat. No. 3,823,138.

[52] U.S. Cl. ............................................... 260/343.3 R
[51] Int. Cl.² ................................................ C07D 307/77
[58] Field of Search ........................................... 260/343.3

[56] References Cited
OTHER PUBLICATIONS

Corey, et al., J. Am. Chem. Soc. 92, pp. 397–398, Jan. 28, 1970.
Corey, et al., JACS 94:4014–4015, (1972).
Corey, et al., JACS 93:1490–1491, (1971).
Corey et al., JACS 91:5675–5677, (1969).

Primary Examiner—Henry R. Jiles
Assistant Examiner—C. M. S. Jaisle
Attorney, Agent, or Firm—Morris L. Nielsen

[57] ABSTRACT

Process for preparing lactones of the formula

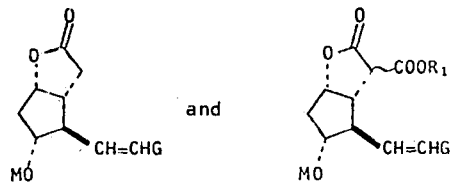

wherein G is $R_9$, 1-hydroxyhexyl, or 1-hydroxy-cis-3-hexenyl, wherein $R_9$ is hydrogen, alkyl of one to 12 carbon atoms, inclusive, cycloalkyl of 3 to 10 carbon atoms, inclusive, aralkyl of 7 to 12 carbon atoms, inclusive, phenyl, or phenyl substituted with one, 2, or 3 alkyl of one to 4 carbon atoms, inclusive; wherein M is hydrogen or a blocking group; wherein $R_1$ is hydrogen, alkyl of one to 12 carbon atoms, inclusive, cycloalkyl of 3 to 10 carbon atoms, inclusive, aralkyl of 7 to 12 carbon atoms, inclusive, phenyl, or phenyl substituted with one, 2, or 3 chloro or alkyl of one to 4 carbon atoms, inclusive, or ethyl substituted in the β-position with 3 chloro, 2 or 3 bromo, or 1, 2, or 3 iodo; and wherein ~ indicates attachment in alpha or beta configuration. The lactones are useful intermediates in preparing prostaglandins having pharmacological utility.

6 Claims, No Drawings

LACTONE INTERMEDIATES

This is a division of application Ser. No. 273,785, filed July 21, 1972, now issued as U.S. Pat. No. 3,823,138.

BACKGROUND OF THE INVENTION

This invention relates to a process for preparing intermediates useful in the preparation of prostaglandins (hereinafter identified as "$PGF_{2\alpha}$", "$PGF_{2\alpha}$", etc.), to certain novel intermediates, and to processes for resolving the optical isomers of those intermediates.

Previously, a racemic bicyclic lactone diol of the formula

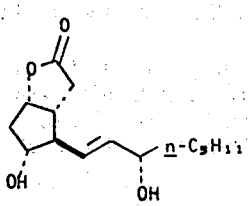

was reported by E. J. Corey et al., J. Am. Chem. Soc. 91, 5675 (1969), and later disclosed in an optically active form by E. J. Corey et al., J. Am. Chem. Soc. 92, 397 (1970). Conversion of this intermediate to $PGE_2$ and $PGF_{2\alpha}$, either in dl-form or optically active form, was disclosed in those publications.

Similarly, an optically active compound of the formula

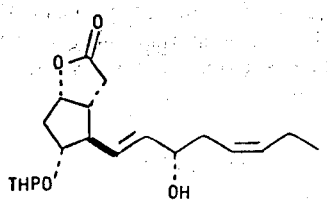

wherein THP is tetrahydropyranyl, and its conversion to $PGE_3$ and $PGF_{3\alpha}$ was reported by E. J. Corey et al., J. Am. Chem. Soc. 93, 1490 (1971).

Subsequent to this invention, the compound

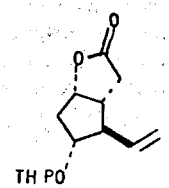

wherein THP is tetrahydropyranyl and the process for making same were reported by E. J. Corey et al., J. Am. Chem. Soc. 94, 4014 (1972).

The known prostaglandins include, for example, prostaglandin $E_2$ ($PGE_2$), prostaglandin $F_2$ alpha and beta ($PGF_{2\alpha}$ and $PGF_{2\beta}$), prostaglandin $A_2$ ($PGA_2$), prostaglandin $B_2$ ($PGB_2$), and the corresponding $PG_3$ compounds. Each of the above-mentioned known prostaglandins is a derivative of prostanoic acid which has the following structure and atom numbering:

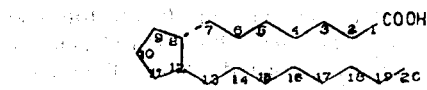

See, for example, Bergstrom et al., Pharmacol. Rev. 20, 1 (1968), and references cited therein. A systematic name for prostanoic acid is 7-[(2β-octyl)-cyclopent-1α-yl]-heptanoic acid.

$PGE_2$ has the following structure:

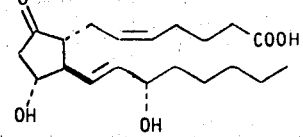

$PGF_{2\alpha}$ has the following structure:

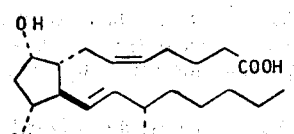

$PGE_3$ has the following structure:

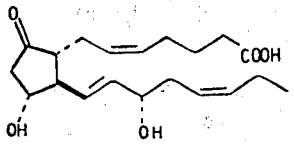

$PGF_{3\alpha}$ has the following structure:

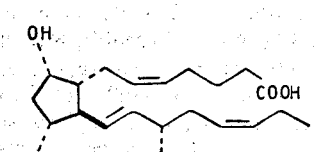

The prostaglandin formulas mentioned above each have several centers of asymmetry. Each formula represents a molecule of the particular optically active form of the prostaglandin obtained from certain mammalian tissues, for example, sheep vesicular glands, swine lung, and human seminal plasma, or by reduction or dehydration of a prostaglandin so obtained. See, for example, Bergstrom et al., cited above, and references cited therein. The mirror image of each formula represents a molecule of the other enantiomeric form of that prostaglandin. The racemic form of the prostaglandin consists of equal numbers of two types of molecules, one represented by one of the above formulas and the other represented by the mirror image of that formula. Thus, both formulas are needed to define a racemic prostaglandin. See Nature 212, 38 (1966) for discussion of the stereochemistry of the prostaglandins.

In the formulas above, as well as in the formulas given hereinafter, broken line attachments to the cyclopentane ring indicate substituents in alpha configuration, i.e., below the plane of the cyclopentane ring. Heavy solid line attachments to the cyclopentane ring indicate substituents in beta configuration, i.e., above the plane of the cyclopentane ring. In the formulas above, the hydroxyl attachment to carbon 15 is in the alpha (or S) configuration, as indicated by the broken line. In formulas below, this convention is also used for intermediates having hydroxyl substitution at the corresponding position on the side chain. A wavy line ∼ indicates optional attachment in either alpha or beta configuration. Reference to the "S" configuration follows the convention used in the art. See for example Nugteren et al., Nature 212, 38 (1966); Cahn, J. Chem. Ed. 41, 116 (1964): and "Basic Principles of Organic Chemistry", J. D. Roberts and M. C. Casero, W. A. Benjamin, Inc., N.Y., 1964, pp. 592–594.

SUMMARY OF THE INVENTION

It is the purpose of this invention to provide novel intermediates useful in the preparation of prostaglandins commercially in substantial amount and at reasonable cost. It is a further purpose to provide processes for preparing these intermediates and for utilizing them.

Thus there is provided an optically active compound of the formula

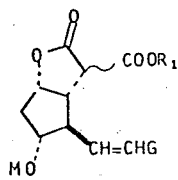

I or a racemic compound of that formula and the mirror image thereof, wherein G is $R_9$, 1-hydroxyhexyl, or 1-hydroxy-cis-3-hexenyl, wherein $R_9$ is hydrogen, alkyl of one to 12 carbon atoms, inclusive, cycloalkyl of 3 to 10 carbon atoms, inclusive, aralkyl of 7 to 12 carbon atoms, inclusive, phenyl, or phenyl substituted with one, 2, or 3 alkyl of 1 to 4 carbon atoms, inclusive; wherein M is hydrogen or a blocking group as defined herein; wherein $R_1$ is hydrogen, alkyl of 1 to 12 carbon atoms, inclusive, cycloalkyl of 3 to 10 carbon atoms, inclusive, aralkyl of 7 to 12 carbon atoms, inclusive, phenyl, or phenyl substituted with 1, 2, or 3 chloro or alkyl of 1 to 4 carbon atoms, inclusive, or ethyl substituted in the β-position with 3 chloro, 2 or 3 bromo, or 1, 2, or 3 iodo; and wherein ∼ indicates attachment in alpha or beta configuration.

There is further provided an optically active compound of the formula

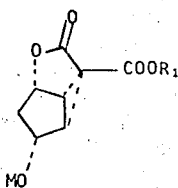

II or a racemic compound of that formula and the mirror image thereof, wherein M and $R_1$ are as defined above.

There is further provided an optically active compound of the formula

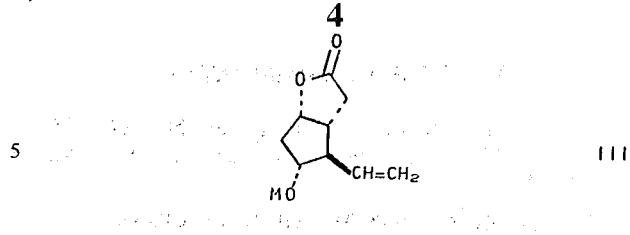

III or a racemic compound of that formula and the mirror image thereof, wherein M is as defined above.

The blocking group is any group which replaces hydrogen of the hydroxyl groups, which is not attacked by nor is reactive to the reagents used in the respective transformations to the extent that the hydroxyl group is, and which is subsequently replaceable by hydrogen at a later stage in the preparation of the prostaglandin-like products.

Several blocking groups are known in the art, e.g. tetrahydropyranyl, acetyl, and p-phenylbenzoyl (see Corey et al., cited above). Those which have been found useful include (a) carboxyacyl of the formula

wherein $R_2$ is

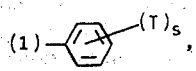

wherein T is alkyl of 1 to 4 carbon atoms, inclusive, phenylalkyl of 7 to 10 carbon atoms, inclusive, or nitro, and s is zero to 5, inclusive, provided that not more than two T's are other than alkyl, and that the total number of carbon atoms in the T's does not exceed 10 carbon atoms;

wherein $R_3$ is alkyl of 1 to 4 carbon atoms, inclusive,

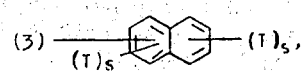

wherein T and s are as defined above, or (4) alkyl of 1 to 4 carbon atoms, inclusive; (b) silyl of the formula $-Si(A)_3$ wherein A is alkyl of 1 to 4 carbon atoms, inclusive, phenyl, phenyl substituted with 1 or 2 fluoro, chloro, or alkyl of 1 to 4 carbon atoms, inclusive, or aralkyl of 7 to 12 carbon atoms, inclusive; (c) tetrahydropyranyl; (d) tetrahydrofuranyl; or (e) a group of the formula

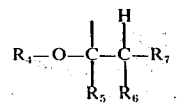

wherein $R_4$ is alkyl of 1 to 18 carbon atoms, inclusive, cycloalkyl of 3 to 10 carbon atoms, inclusive, aralkyl of 7 to 12 carbon atoms, inclusive, phenyl, or phenyl substituted with 1, 2, or 3 alkyl of 1 to 4 carbon atoms, inclusive; wherein $R_5$ and $R_6$ are the same or different, being hydrogen, alkyl of 1 to 4 carbon atoms, inclusive, phenyl, or phenyl substituted with 1, 2, or 3 alkyl of 1 to 4 carbon atoms, inclusive, or, when $R_5$ and $R_6$ are taken together, $-(CH_2)_a-$ or $-(CH_2)_b-O-(CH_2)_c-$ wherein $a$ is 3, 4, or 5, $b$ is 1, 2, or 3, and $c$ is 1, 2, or 3 with the proviso that $b$ plus $c$ is 2, 3, or 4; and wherein $R_7$ is hydrogen or phenyl.

Examples of carboxyacyl include benzoyl; substituted benzoyl, e.g. (2-, 3- or 4-)methylbenzoyl, (2-, 3-, or 4-)ethylbenzoyl, (2-, 3-, or 4-)isopropylbenzoyl, (2-, 3-, or 4-)tert-butylbenzoyl, 2,4-dimethylbenzoyl, 3,5-dimethylbenzoyl, 2-isopropyltoluyl, 2,4,6-trimethylbenzoyl, pentamethylbenzoyl, α-phenyl-(2-, 3-, or 4-)toluyl, 2-, 3-, or 4-phenethylbenzoyl, 2-, 3-, or 4-nitrobenzoyl, (2,4-, 2,5-, or 3,5-)dinitrobenzoyl, 3,4-dimethyl-2-nitrobenzoyl, 4,5-dimethyl-2-nitrobenzoyl, 2-nitro-6-phenethylbenzoyl, 3-nitro-2-phenethylbenzoyl; mono-esterified phthaloyl, e.g.

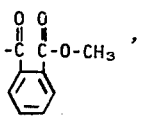

isophthaloyl, e.g.

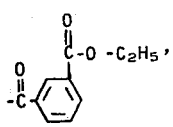

or terephthaloyl, e.g.

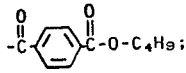

(1- or 2-)naphthoyl; substituted naphthoyl, e.g. (2-, 3-, 4-, 5-, 6-, or 7-)methyl-1-naphthoyl, (2- or 4-)ethyl-1-naphthoyl, 2-isopropyl-1-naphthoyl, 4,5-dimethyl-1-naphthoyl, 6-isopropyl-4-methyl-1-naphthoyl, 8-benzyl-1-naphthoyl, (3-, 4-, 5- or 8-)-nitro-1naphthoyl, 4,5-dinitro-1-naphthoyl, (3-, 4-, 6-, 7- or 8-)methyl-1-naphthoyl, 4-ethyl-2-naphthoyl, and (5- or 8-)nitro-2-naphthoyl; and alkanoyl, e.g. acetyl, propionyl, butyryl, isobutyryl, valeryl, and isovaleryl. Especially preferred are benzoyl and acetyl.

Examples of alkyl of 1 to 4 carbon atoms, inclusive, are methyl, ethyl, propyl, butyl, and isomeric forms thereof. Examples of phenylalkyl of 7 to 10 carbon atoms, inclusive, are benzyl, phenethyl, 1-phenylethyl, 2phenylpropyl, 4-phenylbutyl, and 3-phenylbutyl. Examples of phenyl substituted with 1 or 2 fluoro, chloro, or alkyl of 1 to 4 carbon atoms, inclusive, are p-chlorophenyl, m-fluorophenyl, o-tolyl, 2,4-dichlorophenyl, p-tert-butylphenyl, 4-chloro-2-methylphenyl, and 2,4-dichloro-3-methylphenyl. Examples of aralkyl of 7 to 12 carbon atoms, inclusive, other than the phenylalkyl examples above, are α-naphthylmethyl, and 2-(β-naphthyl)ethyl.

Examples or alkyl of 1 to 12 carbon atoms, inclusive, are, in addition to those alkyl examples above, pentyl, hexyl, heptyl, octyl, nonyl, decyl, undecyl, dodecyl, and isomeric forms thereof. Examples of cycloalkyl of 3 to 10 carbon atoms, inclusive, which includes alkyl-substituted cycloalkyl, are cyclopropyl, 2-methylcyclopropyl, 2,2-dimethylcyclopropyl, 2,3-diethylcyclopropyl, 2-butylcyclopropyl, cyclobutyl, 2-methylcyclobutyl, 3-propylcyclobutyl, 2,3,4-triethylcyclobutyl, cyclopentyl, 2,2-dimethylcyclopentyl, 2-pentylcyclopentyl, 3-tert-butylcyclopentyl, cyclohexyl, 4-tert-butylcyclohexyl, 3-isopropylcyclohexyl, 2,2-dimethylcyclohexyl, cycloheptyl, cyclooctyl, cyclononyl, and cyclodecyl.

Examples of alkyl of 1 to 18 carbon atoms, inclusive, are, in addition to those alkyl examples above, tridecyl, tetradecyl, pentadecyl, hexadecyl, heptadecyl, octadecyl, and isomeric forms thereof. Examples of phenyl substituted with 1, 2, or 3 alkyl of 1 to 4 carbon atoms, inclusive, are (o, m, or p)-tolyl, 3,5-xylyl, (o, m, or p)-ethylphenyl, 2,5-diethylphenyl, (o, m, or p)-butylphenyl, (o, m, or p)-sec-butylphenyl, (o, m, or p)-tert-butylphenyl, 2-isopropyl-3-methylphenyl, 2-ethyl-4-propylphenyl, 2,6-diisopropylphenyl, 3,4,5-trimethylphenyl, and 2,4,6-tributylphenyl.

Especially preferred for $R_1$ are methyl, ethyl, tert-butyl, or β,β,β-trichloroethyl.

The various optically active and racemic prostaglandin products and their salts, esters, alkanoates, and esteralkanoates obtained from the novel intermediates of formulas I, II, and III are useful for various pharmacological purposes. With particular regard to PGF$_2$ α see, for example, Bergstrom et al., Pharmacol. Rev. 20, 1 (1968), and references cited therein, Wiqvist et al., The Lancet, 889 (1970), and Karim et al., J. Obstet, Gynaec. Brit. Cwlth., 76, 769 (1969). As to PGF$_3$ α, for example, see Samuelsson, Biochim. Biophys. Acta 84, 707 (1964).

The prostaglandin end-products obtained from compounds I – III are extremely potent in causing stimulation of smooth muscle as shown, for example by tests on strips of guinea pig ileum, rabbit duodenum, or gerbil colon. Those products are also highly active in potentiating other known smooth muscle stimulators, for example, oxytocic agents, e.g., oxytocin and the various ergot alkaloids including derivatives and analogs thereof. Accordingly, those prostaglandin products are useful in place of or in combination with less than the usual amounts of these and other known smooth muscle stimulators whenever smooth muscle stimulation is needed to alleviate or prevent some physiological condition in mammals, including humans, useful domestic animals, pets, zoological specimens, and laboratory animals, for example, mice, rabbits, rats, and monkeys. For example, those products can be used to alleviate or prevent conditions of gastrointestinal atony in mammals, including humans, e.g., paralytic ileus following anesthesia and surgical operation of from other medical causes. For this purpose, the compound is administered parenterally, e.g., subcutaneously, intramuscularly, or by intravenous injection of infusion in a dose range 0.1 to 2 mg. per kg. of body weight per day, the exact dose depending on the age, weight, and condition of the patient or animals, and the frequency and route of administration. Small repeated doses are indicated when the aim is to prevent rather than alleviate the atony.

Another smooth muscle stimulatory where the prostaglandin obtained from these formula I –III intermediates are useful is in the control or prevention of atonic uterine bleeding in mammals after abortion or delivery, to aid in the expulsion of the placenta, and during the puerperium. For this purpose, the compound is administered by intravenous infusion immediately after abortion or delivery at a dose in the range about 0.1 to about 100 μg. per kg. of body weight per minute until the desired effect is obtained. Subsequent doses are given by intravenous, subcutaneous, or intramuscular injection or infusion during puerperium in the range 0.1 to 2 mg. per kg. of body weight per day, again the exact dose depending on the age, weight, and condition of the patient or animal.

In still another smooth muscle stimulatory area, the prostaglandin products obtained from these formula I–III intermediates are surprisingly useful in place of oxytocin to induce labor in pregnant female animals, including man, cows, sheep, and pigs, at or near term, or in pregnant animals with intrauterine death of the fetus from about 20 weeks to term. For this purpose, the compound is infused intravenously at a dose of 0.1 to 100 μg. per kg. of body weight per minute until at or near the termination of the second stage of labor, i.e., expulsion of the fetus. The compounds are especially useful when the female is 1 or more weeks post-mature and natural labor has not started, or 12 to 60 hours after the membranes have ruptured and natural labor has not yet started. An alternative route of administration is oral.

The prostaglandin products obtained from these formula I–III intermediates are useful for controlling the reproductive cycle in ovulating female mammals, including humans and animals such as monkeys, rats, rabbits, dogs, cattle, and the like. By the term ovulating female mammals is meant animals which are mature enought to ovulate but not so old that regular ovulation has ceased. For that purpose, $PGF_{2\alpha}$, for example, is administered systemically at a dose level in the range 0.1 mg. to about 20 mg. per kg. of body weight of the female mammal, advantageously during a span of time starting approximately at the time of ovulation and ending approximately at the time of menses or just prior to menses. Intravaginal and intrauterine are alternative routes of administration.

Reference to Charts A and B, herein, will make clear the steps for preparing the formula I–III intermediates, useful in producing prostaglandin products, e.g. $PGF_{2\alpha}$ and $PGF_{3\alpha}$ (see Corey et al. citations above).

The 2-cyclopentene-1,4-diol of formula IV is known in the art (see U.S. Pat. No. 2,437,648 issued Mar. 9, 1948, Chemical Abstracts 42, P 4194g).

Referring to the formula-VI compound of Chart A, two routes are employed for its preparation. By one route, shown in Chart A, the formula-V malonate is first prepared from the diol. For this purpose the appropriate chloroformylacetate is employed, e.g. the tert-butyl, ethyl, or β,β,β-trichloroethyl ester, within the scope of the general formula

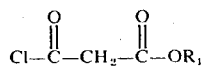

wherein $R_1$ is as defined above. The condensation occurs readily in the presence of a weakly basic tertiary amine such as pyridine, 2,4-(or 2,6-)lutidine, and the like, preferably N,N-dimethylaniline, and goes smoothly at temperatures of −50° C. to +25° C., although higher temperatures may be employed. The reactants are preferably mixed in a solvent such as tetrahydrofuran, dioxane, diethyl ether, benzene, dimethoxyethane, chloroform, dichloromethane, or similar aprotic solvents.

The formula-VI compound wherein M is not hydrogen is then prepared by replacement of the hydrogen atom of the hydroxyl group with a blocking group M'. It is especially desirable that intermediate II have a blocking grout M' to prevent decomposition of the organometallic reagents leading to compound VIII (Chart A) or compound X (Chart B). It is most convenient to prepare compound VI with that blocking group.

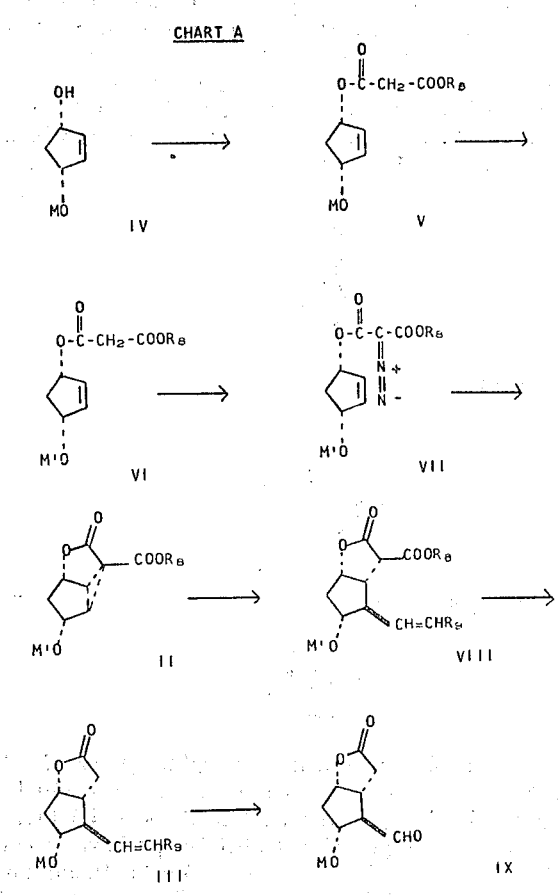

CHART A

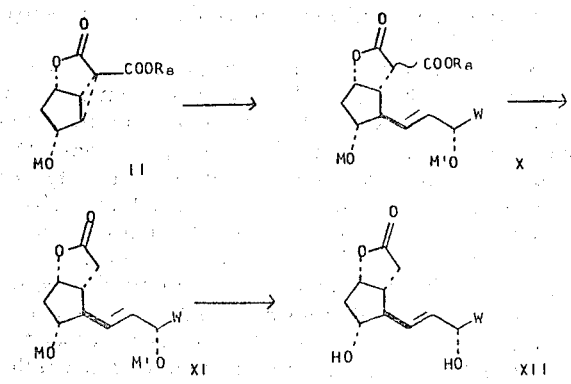

CHART B

In replacing the hydrogen of the hydroxyl group in the 4-position with a carboxyacyl blocking group, methods known in the art are used. Thus, for example benzoic anhydride is reacted with the formula-V compound in the presence of pyridine.

Preferably, however, an acyl halide, for example benzoyl chloride, is reacted with the formula-V compound in the presence of a tertiary amine such as pyridine, triethylamine, and the like. The reaction is carried out under a variety of conditions using procedures generally known in the art. Generally, mild conditions are employed, e.g. 20°–60° C., contacting the reactants in a liquid medium, e.g. excess pyridine or an inert solvent such as benzene, toluene or chloroform. The acylating agent is used either in stoichiometric amount or in excess. If the acyl chloride is not available, it is made from the corresponding acid and phosphorous pentachloride as is known in the art.

When the blocking group is silyl of the formula —Si(A)$_3$, the formula-V compound is transformed to a silyl derivative of formula VI by procedures known in the art. See, for example, Pierce, "Silylation of Organic Compounds," Pierce Chemical Co., Rockford, Ill. (1968). The necessary silylating agents for these transformations are known in the art or are prepared by methods known in the art. See, for example, Post "Silicones and Other Organic Silicon Compounds," Reinhold Publishing Corp., New York, N.Y. (1949). These reagents are used in the presence of a tertiary base such as pyridine at temperatures in the range of about 0° to +50° C. Examples of trisubstituted monochlorosilanes suitable for this purpose include chlorotrimethylsilane, chlorotriisobutylsilane, chlorotriphenylsilane, chlorotris(p-chlorophenyl)silane, chlorotri-m-tolylsilane, and tribenzylchlorosilane. Alternately, a chlorosilane is used with a corresponding disilazane. Examples of other silyating agents suitable for forming the formula-VI intermediates include pentamethylsilylamine, pentaethylsilylamine, N-trimethylsilyldiethylamine, 1,1,1-triethyl-N,N-dimethylsilylamine, N,N-diisopropyl-1,1,1-trimethylsilylamine, 1,1,1-tributyl-N,N-dimethylsilylamine, N,N-dibutyl-1,1,1-trimethylsilylamine, 1-isobutyl-N,N,1,1-tetramethylsilylamine, N-benzyl-N-ethyl-1,1,1-trimethylsilylamine, N,N,1,1-tetramethyl-1-phenylsilylamine, N,N-diethyl-1,1-dimethyl-1-phenylsilylamine, N,N-diethyl-1-methyl-1,1-diphenylsilylamine, N,N-dibutyl-1,1,1-triphenylsilylamine, and 1-methyl-N,N,1,1-tetraphenylsilylamine.

When the blocking group is tetrahydropyranyl or tetrahydrofuranyl, the appropriate reagent, e.g. 2,3-dihydropyran or 2,3-dihydrofuran, is used in an inert solvent such as dichloromethane, in the presence of an acid condensing agent such as p-toluenesulfonic acid or pyridine hydrochloride. The reagent is used in slight excess, preferably 1.0 to 1.2 times theory. The reaction is carried out at about 20°–50° C.

When the blocking group is of the formula $$R_4-O-\overset{|}{C}(R_5)-CHR_6R_7,$$

as defined above, the appropriate reagent is a vinyl ether, e.g. isobutyl vinyl ether or any vinyl ether of the formula $$R_4-O-\overset{|}{C}(R_5)=CR_6R_7$$

wherein R$_4$, R$_5$, R$_6$, and R$_7$ are as defined above; or an unsaturated cyclic or heterocyclic compound, e.g. 1-cyclohex-1-yl methyl ether

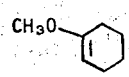

or 5,6-dihydro-4-methoxy-2H-pyran

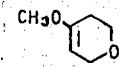

See C. B. Reese et al., J. Am. Chem. Soc. 89, 3366 (1967). The reaction conditions for such vinyl ethers and unsaturates are similar to those for dihydropyran above.

A second route to the formula-VI compounds is by first replacing a hydrogen atom of one of the hydroxyl groups of the cyclopentene diol with a blocking group and thereafter condensing the product with the chloroformylacetate. The conditions for these two steps are essentially the same as discussed above. It is optional which route is employed.

The formula-VII diazomalonate is obtained by replacing the hydrogens of the malonate methylene. For this purpose the formula-VI compound is treated with p-toluenesulfonyl azide in the presence of a tertiary amine, e.g. triethylamine. The reaction is preferably done in a solvent such as acetonitrile. Generally mild conditions are employed, e.g. 20°–30° C. See M. Regitz, Newer Methods of Preparative Organic Chemistry, ed. W. Foerst, Interscience, N.Y., Vol. 6, page 81.

The formula-II tricyclic compound is obtained by cyclization of the diazomalonate using methods known in the art. See, for example, S. Julia et al., C. R. Acad. Sci., Ser. C, 264 (23), 1890 (1969). The cyclization is accomplished at about 100°–150° C., preferably about 125° C., in the presence of copper metal or a copper compound, e.g. copper (I) oxide, copper (I) and copper (II) salts, pentafluorophenylcopper, and copper (I) acetylacetonide. The reaction is conveniently carried out in an organic liquid medium, e.g. hexane or xylene, heated at reflux.

The formula-VIII malonic acid lactone wherein R$_9$ is hydrogen is obtained by reaction of the tricyclic compound with iithiumdivinylcopper or lithiumdivinylcopper complexed with a ligand such as tri-n-butylphosphine, see J. Hooz et al., Can J. Chem. 48, 1626 (1970). The reaction is preferably carried out at low temperature, e.g. below 0° C., in a solvent such tetrahydrofuran. Those compounds wherein R$_2$ is other than hydrogen are prepared by using the appropriate substituted vinylcopper reagent, e.g. (R$_9$CH=CH)$_2$CuLiP(-n—C$_4$H$_9$)$_3$. These reagents are readily obtained from the lithium derivatives of the appropriate vinyl compounds, for example propenyllithium, styryllithium, and the like. These lithium compounds are made by methods known in the art, e.g. by reacting R$_9$CH=CHCl with lithium.

The formula-III lactone is obtained by replacing the R$_1$ group which hydrogen (de-esterification) and decarboxylating. There are several methods of accomplishing this. When a formula-VIII compound is de-esterified in aqueous methanolic potassium hydroxide, for example, the compound is next relactonized by acidification. Thereafter heating at 175°–225° C. yields the formula-III product. Using lithium iodide dihydrate as a reagent (see Fieser et al., Reagents for Organic Synthesis, John Wiley and sons, Inc., N.Y., 1967, p. 617) and heating in 2,4,6-collidine, de-esterification and decarboxylation are both achieved. Wherein R$_1$ is tert-butyl, it is sufficient to merely heat the formula- VIII compound, e.g. in refluxing decalin, to release carbon dioxide and isobutylene. If desired, a catalyst such as lithium iodide may be used.

Where $R_1$ is ethyl substituted in the β-position with 3 chloro, 2 or 3 bromo, 1, 2, or 3 iodo, e.g. β,β,β-trichloroethyl, the group is de-esterified simply by contacting with zinc metal and an alkanoic acid of 2 to 6 carbon atoms, preferably acetic acid. Zinc dust is preferred as the physical form of the zinc. Mixing the haloethyl ester with the zinc dust at about 25° C. for several hours usually causes substantially complete replacement of the haloethyl moiety with hydrogen. The free acid is then isolated from the reaction mixture by procedures known in the art, for example extraction.

In the de-esterification step, certain of the blocking groups, e.g. carboxyacyl and silyl, may be replaced with hydrogen, depending upon the reagents and conditions employed for de-esterification. Therefore, formulas III and IX in Chart A are shown with M to include hydrogen as well as the blocking group.

The formula-IX aldehyde is obtained by ozonization and hydrogenation, using methods known in the art. For example, a solution of the formula-III compound in ethyl acetate is treated with an oxygen-ozone stream at about −75° C., and is thereafter hydrogenated at low pressure with a palladium catalyst.

The formula-IX aldehyde is readily transformed to $PGF_{2\alpha}$ or $PGF_{2\alpha}$ by the processes reported by Corey et al., cited above.

Referring to Chart B, the formula-X compound is obtained by using the appropriate vinylcopper reagent. Thus, when W is pentyl, the formula-II compound is treated with the (tri-n-butylphosphine)copper complex obtained with 3(S)-(α-ethoxy)ethoxy-1-lithio-1-trans-octene (C. J. Sih et al., J. Am. Chem. Soc. 94, 3643 (1972). There is thereby produced the formula-I compound wherein G is 1-hydroxyhexyl and wherein the stereochemistry of the hydroxy-bearing carbon atoms is the sme as in natural prostaglandins. Thereafter, by de-esterification and decarboxylation, the formula-XI compound is obtained, and thence, using methods known in the art, the formula-XII diol useful for producing $PGF_{2\alpha}$ (Corey et al., cited above).

When W in formula X is cis-2-pentenyl, i.e.

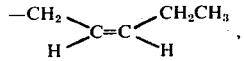

the formula-II compound is reacted with the (tri-n-butylphosphine)copper complex obtained with 1-lithio-3(S)-tetrahydropyranyloxy-1-trans-5-cis-octadiene. Following the steps of Chart B, there are obtained the corresponding formula-X compound, i.e. the formula-I compound wherein G is 1-hydroxy-cis-3-hexenyl,

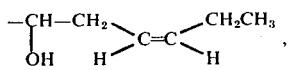

and thence the formula XII diol useful for producing $PGF_{3\alpha}$ (Corey et al., cited above).

The various blocking groups M and M' within the scope as defined herein are selected for convenience in attachment and removal, such selection offering considerable flexibility in the conditions employed in the process steps described above. Preferred for M in Charts A and B are benzoyl and substituted benzoyl; preferred for M' in Chart B are tetrahydropyranyl and (α-ethoxy)ethyl.

When M or M' is carboxyacyl, e.g. benzoyl, replacement with hydrogen is readily achieved by contacting the formula-XI compound with an alkali metal carbonate, for example potassium carbonate, in methanol at about 25° C. When M or M' is silyl, these groups are readily removed by hydrolysis, using procedures known in the art for transforming silyl ethers to alcohols. See, for example, Pierce, cited above, especially p. 447 thereof. A mixture of water and sufficient of a water-miscible organic diluent to give a homogeneous hydrolysis reaction mixture represents a suitable reaction medium. Addition of a catalytic amount of an organic or inorganic acid hastens the hydrolysis. The length of time required for the hydrolysis is determined in part by the hydrolysis temperature. With a mixture of water and methanol at 25° C., several hours is usually sufficient for hydrolysis. At 0° C., several days is usually necessary.

When M or M' is tetrahydropyranyl or similar group including those derived from vinyl ethers, hydrolysis is achieved with methanol-HCl or with acetic acid/water/tetrahydrofuran at 40°–55° C.

In all of the above-described reactions, the products are separated by conventional means from the starting materials and impurities, for example by silica gel chromatography monitored by thin-layer chromatography (TLC).

Optically active compounds are obtained from optically active intermediates according to the process steps of Chart A. Likewise, optically active products are obtained by the transformations of optically active compounds following the processes of Chart B. When racemic intermediates are used in reactions coresponding to the processes of Charts A–B, inclusive, and racemic products are obtained, these racemic products may be used in their racemic form or, if preferred, they may be resolved as optically active isomers, as discussed hereinafter.

Referring to Chart B, when a formula-X compound is prepared by reacting a racemic compound corresponding to formula II with a racemic vinylcopper reagent, e.g. (α-ethoxy)ethoxy-1-lithio-1-trans-octene complex with (tri-n-butylphosphine)copper, there are obtained two pairs of racemates which are separable into pairs of racemic compounds by methods known in the art, e.g. silica gel chromatography. When a racemic compound corresponding to formula II is reacted with an optically active isomer of the vinylcopper reagent, e.g. the 3(S) form (see C.J. Sih, cited above), there are obtained two diastereomers corresponding to the formula-X compound which are separated by conventional methods, e.g. by silica gel chromatography.

It is preferred that the formula-II compound be used in the optically active form which will lead to a prostaglandin product of the natural configuration. For this purpose two resolution processes area available: refer to Charts C and D.

Referring to Chart C, the racemic compound corresponding to formula XIII is first subjected to alkaline hydrolysis to open the lactone ring. Contact with aqueous alkali metal hydroxide, e.g. 10% sodium hydroxide, at about 25° C. accomplishes this readily. At least 1 mole, preferably 1.1 moles, of base are used for each mole of lactone. Thereafter the mixture is acidified and extracted in the carboxy acid form. The racemic acid is reacted with an optically active base, e.g. brucine or strychnine, or preferably ephedrine, to give a mixture of two disastereomeric salts which are separated by known procedures, e.g. fractional crystallization. The salts are then acidified to yield the respective optically active lactones corresponding to formula XIII. For the process of Chart C, the compound corresponding to formulas XIV or XV can not have

CHART C

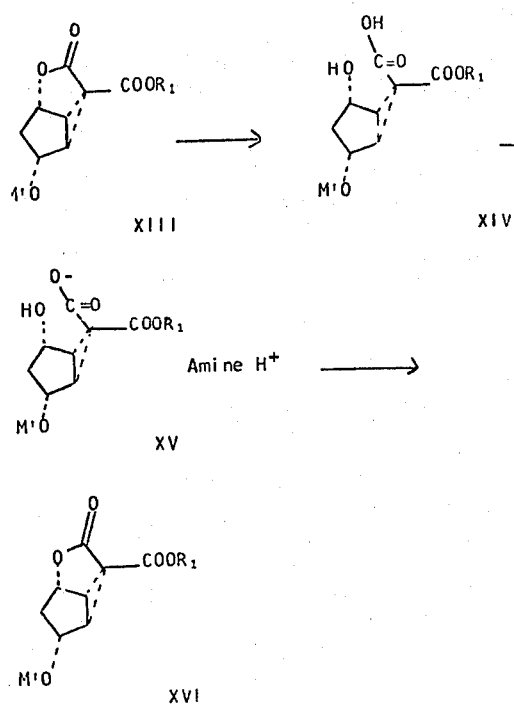

CHART D

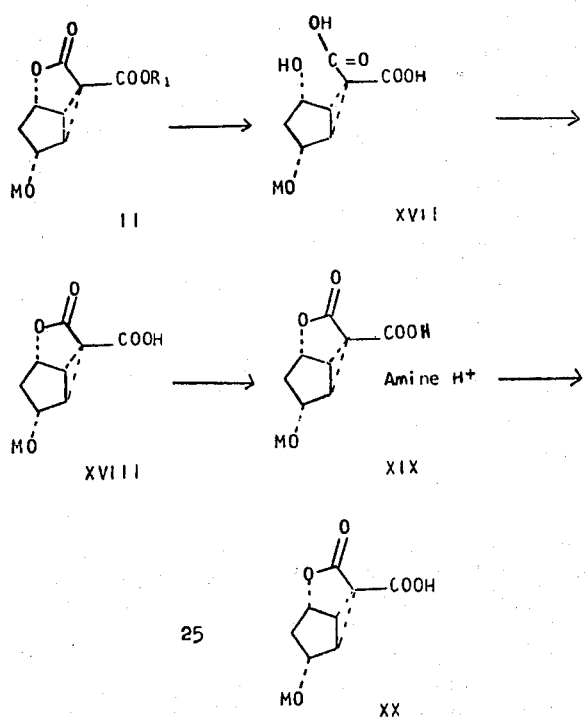

two unsubstituted hydroxy groups. Therefore M' shown, excluding hydrogen. If it is desired that M' of the resolved compound corresponding to formula XVI be replaced by hydrogen, that can be done by methods known in the art or disclosed herein.

Referring to Chart D, in the alternate process of resolution, the racemic compound corresponding to formula 11 is subjected to alkaline hydrolysis to de-esterify $R_1$ and to open the lactone ring. For this purpose the compound is contacted with excess alkai metal hydroxide, e.g. 10% sodium hydroxide, at about 25° C., until the opened lactone dicarboxylic salt corresponding to formula XVII is formed. The compound is acidified to relactonize it and form the free acid corresponding to formula XVIII. The compound is preferably extracted from the aqueous system into an immiscible organic solvent, dried, and then reacted with an optically active base, as above, to give a mixture of two diastereomeric salts which are separated and subsequently acidified to yield the optically active lactones corresponding to formula XX. For the transformations shown in Charts A and B, the free carboxyl of the formula-XX compound is esterified, replacing hydrogen with $R_8$ by methods known in the art.

Optionally, instead of resolving the racemic compounds corresponding to formula II, those corresponding to formulas IV, V, VI and VII (Chart A) are resolved by methods known in the art.

DESCRIPTION OF THE PREFERRED EMBODIMENTS

The invention can be more fully understood by the following examples.

All temperatures are in degrees centigrade.

Infrared absorption spectra are recorded on a Perkin-Elmer model 421 infrared spectrophotometer. Except when specified otherwise, undiluted (neat) samples are used.

NMR spectra are recorded on a Varian A-60 spectrophotometer in deuterochloroform solutions with tetramethylsilane as an internal standard (downfield).

"Brine", herein, refers to an aqueous saturated sodiumchloride solution.

Preparation 1 tert-Butyl Chloroformylacetate,

There is first prepared tert-butyl hydrogen malonate following the procedure of C. R. Hauser et al, J. Am. Chem. Soc. 68, 27 (1946).

Thereafter, following the procedure of D. S. Breslow et al., J. Am. Chem. Soc. 66, 1286 (1944), using phthalyl chloride, the title compound is prepared.

EXAMPLE 1 di-tert-Butyl 4α-Hydroxy-2-cyclopenten-1α-yl Malonate (corresponding to Formula V. M is hydrogen and $R_8$ is tert-butyl)

Refer to Chart A.

A solution of 2-cyclopentene-cis-1,4-diol (0.5 g.) and N,N-dimethylaniline (0.765 g.) in 4 ml. of tetrahydrofuan (THF) is cooled to 0° C. and treated dropwise with tert-butyl (chloroformyl)acetate (Preparation 1, 0.9 g.) over a period of 1 hour. The mixture is concentrated under reduced pressure and the residue is taken up in diethyl ether. The ether solution is extracted with water to remove the amine salt. Then the ether solution is extracted with water several times to remove the desired product, leaving the coformed 1,3-diester in the ether. The combined aqueous layers are saturated with sodium chloride and extracted with dichloromethane. The organic phases is dried over sodium sulfate and concentrated to the formula-V title compound.

EXAMPLE 2 di-tert-Buytl 4α-Acetyloxy-2-cyclopenten-1α-yl Malonate (corresponding to Formula VI: M' is acetyl and $R_8$ is tert-butyl)

Refer to Chart A.

To a mixture of the formula-V tert-butyl 4α-hydroxy-2-cyclopenten-1α-yl malonate (Example 1, 0.5 g.) and 1 ml. of pydridine is added 0.5 ml. of acetic anhydride. After about 30 min. there is added about 30 ml. of ice-water mixture and the mixture is stirred for 30 min. The mixture is acidified to pH 2 with 10% $H_2SO_4$ and extracted with dichloromethane. The organic phase is washed with water, cold 5% sodium bicarbonate and brine, dried over sodium sulfate, and concentrated to the title compound.

EXAMPLE 3 di-tert-Butyl 4α-Acetyloxy-2-cyclopenten-1α-yl Diazomalonate (corresponding to Formula V:11: M' is acetyl and $R_8$ is tert-butyl).

Refer to Chart A.

A solution of the formula-VI tert-butyl 4α-acetyloxy-2-cyclopenten-1α-yl malonate (Example 2, 2.82 g.) and 1.4 ml. of triethylamine in 10 ml. of acetonitrile is treated with tosyl azide (p-toluenesulfonyl azide, Org. Syn. 48, 36 (1968), 2.17 g.) in an additional 4 ml. of acetonitrile. After standing at 25° C. for about 18 hrs., the mixture is concentrated under reduced pressure. The residue is taken up in 20 ml. of diethyl ether and shaken with 18.9 ml. of potassium hydroxide solution containing about 0.51 g. of potassium hydroxide. The organic phase is washed with water and concentrated to yield the title compound.

EXAMPLE 4 di-endo-2-Acetyloxy-6-(tert-butoxycarbonyl)-endo-4-hydroxybicyclo[3.1.0]hexan-6-carboxylic Acid, γ-Lacitone (corresponding to Formula II; M' is acetyl and $R_8$ is tert-butyl)

Refer to Chart A.

A solution of the formula-VII tert-butyl 4α-acetyloxy-2-cyclopenten-1α-yl diazonalonate (Example 3, 1.5 g.) in xylene is mixed with copper powder (0.5 g.) and heated at reflux for 6 hrs. The solids are filtered off and the solution is concentrated under reduced pressure. The residue is chromalographed on a silica gel column and those fractions shown by TLC to contain the desired product free of starting material and impurities are combined and concentrated to yield the title compound.

EXAMPLE 5

Resolution of endo-2-Acetylox-6-(tert-butoxycarbony)-endo-4-hydroxybicyclo[3.1.0]hexane-6-carboxylic Acid, γ-Lactone Refer to Chart C.

A. A solution of the formula-II compound (Example 4) in 1.1 mole equivalents of 10% sodium hydroxide is left until the starting material is completely transformed to the opened lactone salt. The solution is carefully acidified to pH 4.0 and thereafter extracted with ethyl acetate. The organic phase is dried with magnesium sulfate and treated with 1-ephedrine to form the ephendrine salt, which is recovered from the ethyl acetate on concentrating and cooling. The salt is recrystallized from ethyl acetate to yield one of the two diastereomeric salts.

A solution of the above salt in chloroform is treated with a mole equivalent of hydrochloric acid, and the mixture is concentrated under reduced pressure. Water is added and the mixture is extracted with benzene. The organic phase is dried and concentrated to yield an otpically active isomer of the title compound, called "the isomer of Example 5-A" herein.

B. following the procedure of Part A above, but replacing 1-ephedrine with d-ephedrine, there is obtained another diastereomeric salt which yields, with hydrochloric acid, an enantiomer of the isomer of Part A, called "the isomer of Example 5-B" herein.

EXAMPLE 6

Resolution of endo-2,4-Dihydroxybicyclo[3.1.0]hexane-6,6-dicarboxylic acid, γ-Lacetone Refer to Chart D.

A. A solution of the formula-II endo-2-acetyloxy-6-(tert-butoxycarbonyl)-endo-4-hydroxybicyclo[3.1.0-]hexane-6-carboxylic acid, γ-lactone (Example 4) in an excess of 10% sodium hydroxide is left until the starting material is transferred to the opened lactone dicarboxylic salt. The solution is carefully acidified to pH 4.0 and after standing is extracted with ethyl acetate. The organic phase is dried with magnesium sulfate and treated with 1-ephedrine to form the ephedrine salt which is recovered from the ethyl acetate on concentrating and cooling. The salt is recrystallized from ethyl acetate to yield one of the two diastereometric salts.

A solution of the above salt in ethyl acetate is treated with a mole equivalent of hydrochloric acid, and the mixture is partially concentrated under reduced pressure. Water is added and the mixture is separated with ethyl acetate. The organic phase is dried and concentrated to yield an optically active isomer of the title compound. called "the isomer of Example 6-A" herein.

B. Following the procedure of Part A above, but replacing 1-ephedrine with d-ephedrine, there is obtained another diastereomeric salt which yields, with hydrochloric acid, an enantiomer of the isomer of Part A, called "the isomer of Example 6-B" herein.

EXAMPLE 7

3α-Acetyloxy-5α-hydroxy-2α-vinyl-1α-cyclopentanemalonic Acid, γ-Lactone, tert-Butyl Ester (Formula VIII: M' is acetyl $R_8$ is tert-butyl, and $R_8$ is hydrogen)

Refer to Chart A.

Following the procedure of J. Hooz and R. G. Layton, Can. J. Chem. 48, 1626 (1970), there is prepared a tetrahydrofuran solution of 2.5 mM. of divinylcopperlithium tri-n-butylphosphine complex, $(CH_2=CH)_2CuLiP(n-C_4H_9)_3$ from vinyllithium and tetrakis[iodo(tri-n-butylphosphine)copper(i)]. To that solution at about −78° C. is then added a solution of the formula-II endo-2-acetyloxy-6-(tert-butoxycarbonyl)- endo-4-hydroxybicyclo[3.1.0]hexane-6-carboxylic acid, γ-lactone (isomer of Example 5-A, 0.486 g.) in tetrahydrofuran. The mixture is left to warm slowly to 0° C. over 2 hrs. and is then added to a saturated ammonium chloride solution. The mixture is extracted 3 times with diethyl ether, and the combined organic phase is dried over sodium sulfate and concentrated under reduced pressure. The residue is chromatographed over silica gel.

Similarly using the isomer of Example 5-α and following the above procedure, there is obtained a second product. Thus are prepared the formula-VIII title compound and its enantiomer.

In the manner, using the racemic product of Example 4, and following the above procedure, there is obtained the racemic product corresponding to formula VIII.

EXAMPLE 8

3α-cyclopentaneacetic Acid γ-Lactone (Formula III: M is acetyl and $R_8$ is hydrogen)

Refer to Chart A.

Each of the enantiomeric products corresponding to the formula-VIII 3α-acetyloxy-5α-hydroxy-2α-vinyl-(β-cyclopentanemalonic acid, γ-lactone-tert-butyl ester (Example 7) is dissolved in decaline and heated at reflux. After evolution of gas ceases, the mixture is cooled and concentrated to yield the respective compound corresponding to formula III.

In like manner, employing the racemic product obtained following Example 7, there is obtained the racemic product corresponding to formula III.

EXAMPLE 9

3α-Acetyloxy-2β-carboxaldehydr-5-α-hydroxycyclopentaneacetic Acid γ-Lactone (Formula IX M is acetyl)

Refer to Chart A.

Each of the enantiomeric products corresponding to the formula-III 3α-acetyloxy-5α-hydroxy-2β-cyclopentaneacetic acid γ-lactone (Example 8, 0.200 g.) is dissolved in 20 ml. of ethyl acetate and cooled to about −75° C. The solution is treated with an oxygen stream containing ozone until the starting material has been consumed, as shown by TLC. The mixture is warred to about 25° C., treated with 5% palladium-on-carbon (0.1 g.), and hydrogenated at 20 psi for about 1 hours. The solids are filtered off and the filtrate concentrated under reduced pressure. The residue is chromatographed on silica gel to yield the respective compound corresponding to formula IX. One of the enantiomers is found to yield a prostaglandin having the natural configuration (Corey et al, J. Am. chem. Soc. 92, 387 (1970).

In like manner, employing the racemic product following Example 8, there is obtained the racemic product corresponding to formula IX.

EXAMPLE 10

3α-Bennzoyloxy -5α-hydroxy-2β-[3(S)-(α-ethoxy)-ethoxy-1-trans-octenyl]-1α-cyclopentane-malonic Acid, γ-Lactone, tert-Butyl Ester (Formula X: M is benzoyl, M′ is (α-ethoxy)-ethyl, $R_1$ is tert-butyl, and W is pentyl)

Refer to Chart B.

A. There is first prepared the di-endo-2-benzoyloxy-6-(tert-butoxycarbonyl)-endo-4-hydroxybicyclo[3.1.0-]hexane-6-carboxylic acid, γ-lactone corresponding to formula-II. To a mixture of the di-tert-butyl 4α-hydroxy-2-cyclopenten-1α-yl malonate (Example 1, 0.5 g.) and 1 ml. of pyridine is added 0.5 ml. of benzoyl chloride. After about 30 min., 10 ml. of toluene is added and the mixture concentrated under reduced pressure. The residue is dissolved in ethyl acetate, washed with cold 10% sulfuric acid, brine, aqueous saturated sodium bicarbonate, and brine. The organic phases is dried over sodium sulfate and concentrated to yield the racemic benzoyloxy compound corresponding to formula VI.

Following the procedures of Example 3 and 4, the product of Part A above is transformed to the corresponding formula-VII compound and thence to the desired racemic compound corresponding to formula II.

B. Following the procedure of Example 5, the racemic compound corresponding to formula II is resoled into two enantiomers.

C. To a solution of each of the enactiomeric products of Part B above (0.5 g.) in diethyl ether, previously cooled to 0° C., is added one molar equivalent of tri-n-butylphosphinecopper (1) iodide complex (G. B. Iaufman et al., Inorg. syn. 7, 9 (1963). There is then added two molar equivalents of 3(S)-(α-ethoxy)ethoxy-1-lithio-1-transoctene (C. J. Sih et al., J. Am. Chem. Soc. 94, 3643 (1972) and the mixture is kept at about 0° C. for 1 hour. The mixture is added to saturated aqueous ammonium chloride solution and extracted with diethyl ether. The organic phase is dried over sodium sulfate and concentrated. The residue is chromatographed on silica gel, combining those fractions shown by TLC to be free of starting material and impurities, and concentrating to yield the benzoyloxy compound of formula X and its enantiomer.

In like manner, following the procedure of step C, but employing the racemic product corresponding to formula II from step A, there is obtained the racemic product corresponding to formula X.

EXAMPLE 11

3α-Benzoyloxy-5α-hydroxy-2β-]3(S)-(α-ethoxy)-ethoxy-1-trans-octenyl]-1α-cyclopentaneacetic Acid, γ-Lactone (Formula XI: M is benzoyl, M′ is (α-ethoxy)ethyl, and W is pentyl)

Refer to Chart B.

Following the procedure of Example 8 but replacing the acetyloxy compound of that example with the enantiomeric benzoyloxy compounds of Example 10, there are obtained, separately, the title compound and its enantiomer.

In the manner, employing the racemic benzoyloxy compound following Example 10, there is obtained the racemic product corresponding to formula XI.

EXAMPLE 12

3α-, 5α-Dihydroxy-2β-[3(S)-hydroxy-1 -transoctenyl]-1α-cyclopentaneacetic Acid, γ-Lactone (Formula XII: W is pentyl)

Refer to Chart B.

A solution of the formula-XI compound of Example 11 (0.3 g.) in 10 ml. of methanol is stirred with potassium carbonate (0.1 g.) at about 25° C. for one hour. Thereafter, 8 ml. of chloroform is added, the mixture is filtered, and the organic phase is concentrated under reduced pressure. The residue is taken up in 5 ml. of aqueous tetrahydrofuran (50%) and 50 mg. of p-toluenesulfonic acid is added. The mixture is maintaine at about 25° C. for 2 hrs. and solvent is removed under reduced pressure. Dichloromethane is added and washed with 5% sodium bicarbonate and water. The solution is dried over sodium sulfate and concentrated. The residue is chromatographed over silica gel, and those fractions shown by TLC to be free of starting material and impurities are combined and concentrated to yield the title compound.

In like manner, employing the racemic product following Example 11, there is obtained the racemic product corresponding to formula XII.

EXAMPLE 13

3α-Benzoyloxy-5α-hydroxy-2β-[3(S)-tetrahydropyranyloxy-trans-1-cis-5-octadienyl]-(α-cyclopentanemalonic Acid, γ-Lactone, tert-Butyl Ester (Formula X: M is benzoyl, M' is tetrahydropyranyl, W is cis-2-pentenyl, and $R_1$ is tert-butyl)

Refer to Chart B.

A. There is first prepared 1-lithio-3(S(-tetrahydropyranyloxy-1-trans-5-cis-octadine. The (S)-(+)-phosphonium iodide of the formula

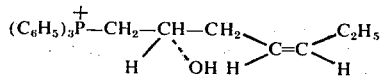

(E. J. Corey et al.,) J. Am. Chem. Soc. 93, 1490 (1971). herein identiied as 2α-hydroxy-4-heptenyltriphenylphosphonium iodide, dissolved in tetrahydrofuran is treated at −20° C. with 2 mole equivalents of n-butyllithium added dropwise. Thereafter one mole equivalent of dichloromethane is added and the mixture is warmed to about 25° C. The mixture is added to water and the organic phase is separated, washed with water, dried over sodium sulfate, and concentrated. The 1-chloro-3(S)-tetrahydropyranyloxy-trans-1-cis-5-octadiene intermediate is isolated by chromatography on a silica gel column, combining and concentrating those fractions shown by TLC to be free of starting materials and impurities. Treatment of the 1-chloro compound with lithium metal in tetrahydrofuran [R. West et al., J. Org. Chem., 26, 2096 (1961)] gives the desired 1-lithio compound.

B. Following the procedure of Example 10B, but replacing 3(S)-(α-ethoxy)ethoxy-1-lithio-1-trans-octene of that example with two mole equivalents of the 1-lithio product of Part A, above, and finally chromatographing the product of silica gel, there is obtained the title compound.

In like manner, using racemic reactants, there is obtained the racemic product corresponding to the above formula-X title compound.

EXAMPLE 14

3α,5α-Dihydroxy-2β-[3(S)-hydroxy-trans-1-cis-5-octadienyl]-1α-cyclopentaneacetic Acid γ-Lactone (Formula XII: W is cis-2-pentenyl)

Refer to Chart B.

Following the procedures of Examples 11 and 12, but replacing the formula-X benzoyloxy compound of Example 11 with the formula-X product of Example 13, there is obtained the title compound.

In like manner, using the racemic product following Example 13, there is obtained the racemic product corresponding to the formula-XII title compound.

EXAMPLE 15 endo-5α-Hydroxy-3α-trimethylsilyloxy-2β-vinyl-1α-cyclopentanemalonic Acid, γ-Lactone, Ethyl Ester (Formula VIII: M' is trimethylsilyl and $R_1$ is ethyl)

Refer to Chart A.

A. dl-Ethyl 4α-hydroxy-2-cyclopenten-1α-yl malonate.- Following the procedure of Example 1 but replacing tert-butyl (chloroformyl)acetate of that example with ethyl malonyl chloride (D. S. Breslow et al., J. Am. Chem. Soc. 66, 1286 (1944), the compound corresponding to formula-V is obtained as an oil, 0.5 g., having NMR peaks at 1.22, 1.50, 1.75, 2.65, 2.88, 3.30 (singlet), 4.16, 4.67, 5.50, and 6.01 δ; and having infrared absorption bands at 3420 and 1730 cm$^{-1}$.

B. dl-Ethyl 4α-trimethylsilyloxy-2-cyclopenten-1α-yl malonate. A solution of the product of Part A, above, (1.508 g.) in 15 ml. of tetrahydrofuran is treated with 3 ml. of hexamethyl disilazane and 0.17 ml. of trimethylchlorosilane at 23° C. for 1.5 hr. The mixture is concentrated under reduced pressure and the residue taken up in benzene. The mixture is filtered and the filtrate concentrated to the compound corresponding to formula-VI, an oil, 2.24 g., having NMR peaks at 0.12, 1.24, 1.50, 1.73, 2.68, 2.91, 3.31 (singlet), 4.19, 4.70, 5.51, and 5.93 δ.

C. dl-Ethyl 4α-trimethylsilyloxy-2-cyclopenten-1α-yl diazomalonate. Following the procedure of Example 3 but replacing the formula-VI compound of that example with the product of Part B, above, there is obtained the compound corresponding to formula-VII as an oil, having NMR peaks at 0.16, 1.32, 1.57, 1.80, 2.75, 2.98, 4.31, 4.75, 5.62, and 5.98 (singlet) δ.

Following the procedure of Example 4, but replacing the formula-VII compound of that Example with the product of Part C above, there is obtained the corresponding formula-II 3α-trimethylsilyloxy intermediate. Following the procedure of Example 6, the formula-II intermediate is obtained as two enantiomers. Each is silylated by the procedures described herein (Example 15-β) to obtained the respective formula-II silylated intermediate. Thereafter, following the procedure of Example 7, these enantiomers are transformed to compound VIII and its enantiomer.

EXAMPLE 16 dl-endo-5α-Hydroxy-3α-tetrahydropyranyloxy-2β-vinyl-1α-cyclopentanemalonic Acid, γ-Lactone, Ethyl Ester (corresponding to Formula VIII: M is tetrahydropyranyl and $R_1$ is ethyl)

Refer to Chart A.

A. dl-ethyl 4α-tetrahydropyranyloxy-2-cyclopenten-1α-yl malonate. A solution of the formula-V dl-ethyl 4α-hydroxy-2-cyclopenten-1α-yl malonate (Example 15-A, 1.5 g.) in 15 ml. of dichloromethane is treated with 3.0 ml. of dihydropyran in the presence of pyridine hydrochloride (10 mg.). The reaction mixture is washed with dilute aqueous potassium bicarbonate, dried, and concentrated to the formula VI compound, having NMR peaks at 1.28, 1.65, 2.86, 3.36, 4.21, 4.7, 5.67, and 6.06 δ; infrared absorption at 1730 and 1750 cm$^{-1}$.

B. dl-ethyl 4α-tetrahydropyranyloxy-2-cyclopenten-1α-yl malonate. A solution of the 3.82 g. formula-VI compound from part A (3.82 g.), of triethyl amine (1.27 g.); and of p-toluenesulfonyl azide (2.91 g.) in 20 ml. of acetonitrile is stirred at about 25° C. for 16 hrs.

The solvent is removed under vacuum. The residue is dissolved in 40 ml. of ether and washed with 26.6 ml. of aqueous potassium hydroxide (0.845 g.) and with water until neutral. The organic layer is dried over sodium sulfate and concentrated to the formula-VII compound as an oil having NMR peaks at 1.32, 1.63, 2.87, 4.31, 4.7, 5.63, and 6.08 δ; infrared absorption at 2140, 1745, and 1727 cm$^{-1}$.

C. Following the procedures of Examples 4 and 7, but replacing the formula-VII compound of Example 4 with the product of Step B above, there is obtained, first, the corresponding figure-II compound, dl-endo-2-tetrahydropyranyloxy-6-(ethoxycarbonyl)-endo-4-hydroxybicyclo[3.1.0]hexane-6-carboxylic acid, -lactone, having NMR peaks at 4.9, 4.7, 4.25, 3.0–4.0, 2.1, 1.6, and 1.3 δ, and having infrared absorption bands at 1780, 1723, and 2940 cm$^{-1}$; and subsequently, the title compound.

I claim:

1. An optically active compound of the formula

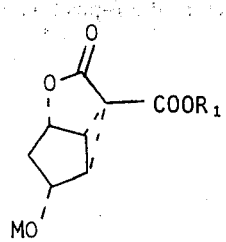

wherein M is carboxyacyl of the formula

wherein $R_2$ is

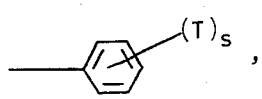

wherein T is alkyl of one to 4 carbon atoms, inclusive, phenylalkyl of 7 to 10 carbon atoms, inclusive, or nitro, and s is zero to 5, inclusive, provided that not more than two T's are other than alkyl, and that the total number of carbon atoms in the T's does not exceed 10 carbon atoms;

wherein $R_3$ is alkyl of one to 4 carbon atoms, inclusive,

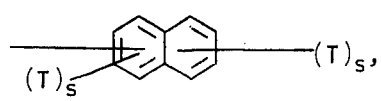

wherein T and s are as defined above, or (4) alkyl of 1 to 4 carbon atoms, inclusive; and wherein $R_1$ is hydrogen, alkyl of 1 to 12 carbon atoms, inclusive, cycloalkyl of 3 to 10 carbon atoms, inclusive, phenylalkyl of 7 to 12 carbon atoms, inclusive, phenyl, or phenyl substituted with 1, 2, or 3 chloro or alkyl of 1 to 4 carbon atoms, inclusive, or ethyl substituted in the β-position with 3 chloro.

2. An optically active compound of the formula

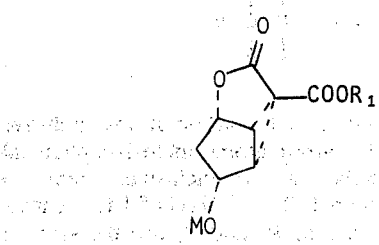

wherein M is silyl of the formula -Si(A)$_3$ wherein A is alkyl of 1 to 4 carbon atoms, inclusive, phenyl, phenyl substituted with 1 or 2 fluoro, chloro, or alkyl of 1 to 4 carbon atoms, inclusive, or phenylalkyl of 7 to 12 carbon atoms, inclusive; and wherein $R_1$ is hydrogen, alkyl of 1 to 12 carbon atoms, inclusive, cycloalkyl of 3 to 10 carbon atoms, inclusive, phenylalkyl of 7 to 12 carbon atoms, inclusive, phenyl, or phenyl substituted with 1, 2, or 3 chloro or alkyl of 1 to 4 carbon atoms, inclusive, or ethyl substituted in the β-position with 3 chloro.

3. An optically active compound of the formula

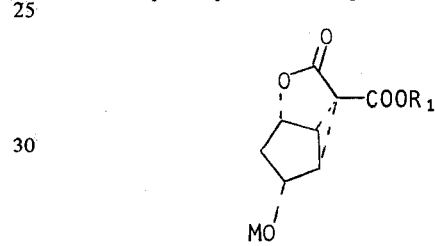

wherein M is tetrahydropyranyl; and wherein $R_1$ is hydrogen, alkyl of 1 to 12 carbon atoms, inclusive, cycloalkyl of 3 to 10 carbon atoms, inclusive, phenylalkyl of 7 to 12 carbon atoms, inclusive, phenyl, or phenyl substituted with 1, 2, or 3 chloro or alkyl of 1 to 4 carbon atoms, inclusive, or ethyl substituted in the β-position with 3 chloro.

4. An optically active compound of the formula

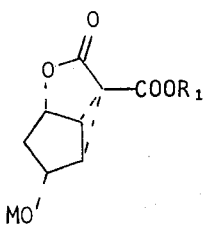

wherein M is tetrahydrofuranyl; and wherein $R_1$ is hydrogen, alkyl of 1 to 12 carbon atoms, inclusive, cycloalkyl of 3 to 10 carbon atoms, inclusive, phenylalkyl of 7 to 12 carbon atoms, inclusive, phenyl, or phenyl substituted with 1, 2, or 3 chloro or alkyl of 1 to 4 carbon atoms, inclusive, or ethyl substituted in the β-position with 3 chloro.

5. An optically active compound of the formula

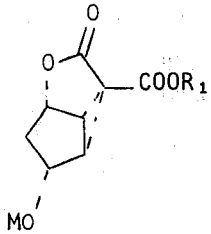

wherein M is a group of the formula

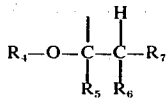

wherein R₄ is alkyl of 1 to 18 carbon atoms, inclusive, cycloalkyl of 3 to 10 carbon atoms, inclusive, phenylalkyl of 7 to 12 carbon atoms, inclusive, phenyl, or phenyl substitued with 1, 2, or 3 alkyl of 1 to 4 carbon atoms, inclusive; wherein $R_5$ and $R_6$ are the same or different, being hydrogen, alkyl of 1 to 4 carbon atoms inclusive, phenyl, or phenyl substituted with 1, 2, or 3 alkyl of 1 to 4 carbon atoms, inclusive, or, when $R_5$ and $R_6$ are taken together, $-(CH_2)_1-$ or $-CH_2-)_b-O-(CH_2)_c-$ wherein $a$ is 3, 4, or 5, $b$ is 1, 2, or 3, and $c$ is 1, 2, or 3 with the proviso that $b$ plus $c$ is 2, 3, or 4; wherein $R_7$ is hydrogen or phenyl; and wherein $R_1$ is hydrogen, alkyl of 1 to 12 carbon atoms, inclusive, cycloalkyl of 3 to 10 carbon atoms, inclusive, phenylalkyl of 7 to 12 carbon atoms, inclusive, phenyl, or phenyl substituted with 1, 2, or 3 chloro or alkyl of 1 to 4 carbon atoms, inclusive, or ethyl substituted in the β-position with 3 chloro.

6. An optically active compound of the formula

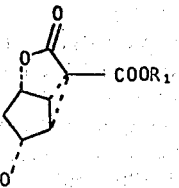

wherein M is hydrogen; and wherein $R_1$ is hydrogen, alkyl of 1 to 12 carbon atoms, inclusive, cycloalkyl of 3 to 10 carbon atoms, inclusive, aralkyl of 7 to 12 carbon atoms, inclusive, phenyl, or phenyl substituted with 1, 2, or 3 chloro or alkyl of 1 to 4 carbon atoms, inclusive, or ethyl substituted in the β-position with 3 chloro.

* * * * *

UNITED STATES PATENT OFFICE
CERTIFICATE OF CORRECTION

Patent No. 3,965,118          Dated June 22, 1976

Inventor(s) Verlan H. Van Rheenen          Page 1 of 2

It is certified that error appears in the above-identified patent and that said Letters Patent are hereby corrected as shown below:

Column 1, line 11, ""PGF$_2\alpha$"" should read -- "PGF$_3\alpha$" --. Column 6, line 51, "of" should read -- or --; line 53, "of" should read -- or --; line 60, "stimulatory where" should read -- stimulatory area where --; line 61, "prostaglandin obtained" should read -- prostaglandin products obtained --.

Column 10, line 47, "R$_2$" should read -- R$_9$ --. Column 11, line 29, "PGF$_2\alpha$" should read -- PGF$_3\alpha$ --; line 32, "vinylcoper" should read --vinylcopper --; lines 39-40, "atoms is the sme" should read -- atom is the same --. Column 12, line 60, "area" should read -- are --. Column 14, line 8, "11" should read -- II --; lines 68-69, "tetrahydrofuan" should read -- tetrahydrofuran --. Column 15, line 10, "phases" should read -- phase --; line 15, "di-" should read -- dl- --; line 32. "di-" should read -- dl- --; line 33, "V:11:" should read -- V:11 --; line 50, "di-" should read -- dl- --; line 52, "Lacitone" should read -- Lactone --; line 57, "diazonalonate" should read -- diazomalonate --; line 61, "chromlographed" should read -- chromatographed --; line 68, "Acetylox" should read -- Acetyloxy --; line 68, "butoxycarbony" should read -- butoxycarbonyl --. Column 16, line 10, "ephendrine" should read -- ephedrine --; line 19, "otpically" should read -- optically --; line 30, "Lacetone" should read -- Lactone --; line 36, "transferred" should read -- transformed --; line 58; "2$\alpha$" should read -- 2$\beta$ --; line 68, "(i)" should read -- (I) --. Column 17, line 10, "5-$\alpha$" should read -- 5-B --; line 14, "the" should read -- like --; line 19, "3$\alpha$-cyclopentane acetic" should read -- 3$\alpha$-acetyloxy-5$\alpha$-hydroxy-2$\beta$-vinyl-1$\alpha$-cyclopentane acetic -- line 21, "R$_8$" should read -- R$_9$ --; line 24, "2$\alpha$" should read -- 2$\beta$ --; line 25, "$\beta$-" should read -- $\alpha$- --; line 26, "decaline" should read -- decalin --; line 35, "carboxaldehydr-5$\alpha$-" should read -- carboxaldehyde-5$\alpha$- --; line 41, "2$\beta$-cyclopentaneacetic" should read -- 2$\beta$-vinyl-1$\alpha$-cyclopentaneacetic --; line 46, "warred" should read -- warmed --; line 54, "387" should read -- 397 --;

UNITED STATES PATENT OFFICE
CERTIFICATE OF CORRECTION

Patent No. 3,965,118    Dated June 22, 1976

Inventor(s) Verlan H. Van Rheenen    Page 2 of 2

It is certified that error appears in the above-identified patent and that said Letters Patent are hereby corrected as shown below:

line 61, "Bennzoyloxy" should read -- Benzoyloxy --; line 67, "di-" should read -- dl- --. Column 18, line 1, "di-" should read -- dl- --; line 9, "phases" should read -- phase --; line 18, "resoled" should read -- resolved --; line 20, "enactiomeric" should read -- enantiomeric --; lines 24 and 25, "laufman" should read -- Kaufman --; line 25, "syn." should read -- Syn. --; line 43, "|3" should read -- [3 --; line 53, "the" should read -- like --;
                                                                  Column 20, lines 20-21, "1.5" should read -- 0.5 --; line 42, "15-β)" should read -- 15-B) --. Column 21, line 14, "-lactone" should read -- $\gamma$-lactone --. Column 23, line 17, "-(CH$_2$)$_1$-" should read -- -(CH$_2$)$_a$- --.

Signed and Sealed this

Eleventh Day of January 1977

[SEAL]

Attest:

RUTH C. MASON
*Attesting Officer*

C. MARSHALL DANN
*Commissioner of Patents and Trademarks*